United States Patent [19]
Platt, Jr.

[11] Patent Number: 6,039,736
[45] Date of Patent: Mar. 21, 2000

[54] SIDE-FIRE COAGULATOR

[75] Inventor: Robert C. Platt, Jr., Boulder, Colo.

[73] Assignee: Sherwood Services AG, Schaffhausen, Switzerland

[21] Appl. No.: 09/162,796

[22] Filed: Sep. 29, 1998

[51] Int. Cl.⁷ .................................................. A61B 17/39
[52] U.S. Cl. .................. 606/49; 219/121.5; 219/121.51; 606/40
[58] Field of Search .................................. 606/49, 40, 45, 606/46; 219/121.5, 121.51

[56] References Cited

U.S. PATENT DOCUMENTS

| | | |
|---|---|---|
| 4,901,719 | 2/1990 | Trenconsky et al. . |
| 5,122,138 | 6/1992 | Manwaring . |
| 5,163,935 | 11/1992 | Black et al. . |
| 5,207,675 | 5/1993 | Canady . |
| 5,242,438 | 9/1993 | Saadatmanesh et al. . |
| 5,248,311 | 9/1993 | Black et al. . |
| 5,292,320 | 3/1994 | Black et al. . |
| 5,366,456 | 11/1994 | Rink et al. . |
| 5,370,649 | 12/1994 | Gardetto et al. . |
| 5,380,317 | 1/1995 | Everett et al. . |
| 5,476,461 | 12/1995 | Cho et al. . |
| 5,496,308 | 3/1996 | Brown et al. . |
| 5,537,499 | 7/1996 | Brekke . |
| 5,620,439 | 4/1997 | Abela et al. . |
| 5,669,907 | 9/1997 | Platt, Jr. et al. . |
| 5,688,261 | 11/1997 | Amirkhanian et al. . |
| 5,700,260 | 12/1997 | Cho et al. . |
| 5,720,745 | 2/1998 | Farin et al. . |

FOREIGN PATENT DOCUMENTS

| | | |
|---|---|---|
| 4326037 | 2/1995 | Germany . |
| 9303678 | 3/1993 | WIPO . |

*Primary Examiner*—Lee Cohen

[57] ABSTRACT

An electrosurgical apparatus for coagulating tissue includes an elongated flexible tube which extends through a working channel of an endoscope. A pressurized ionizable gas is supplied to the proximal end of the tube and is forced at a rate of greater than 1 liter per minute therethrough. The tube also includes at least one aperture located along the periphery of the tube and an angularly disposed surface located within the tube for redirecting the gas through the aperture and at the tissue. At least one electrode ionizes the gas prior to the gas exiting the aperture.

11 Claims, 7 Drawing Sheets

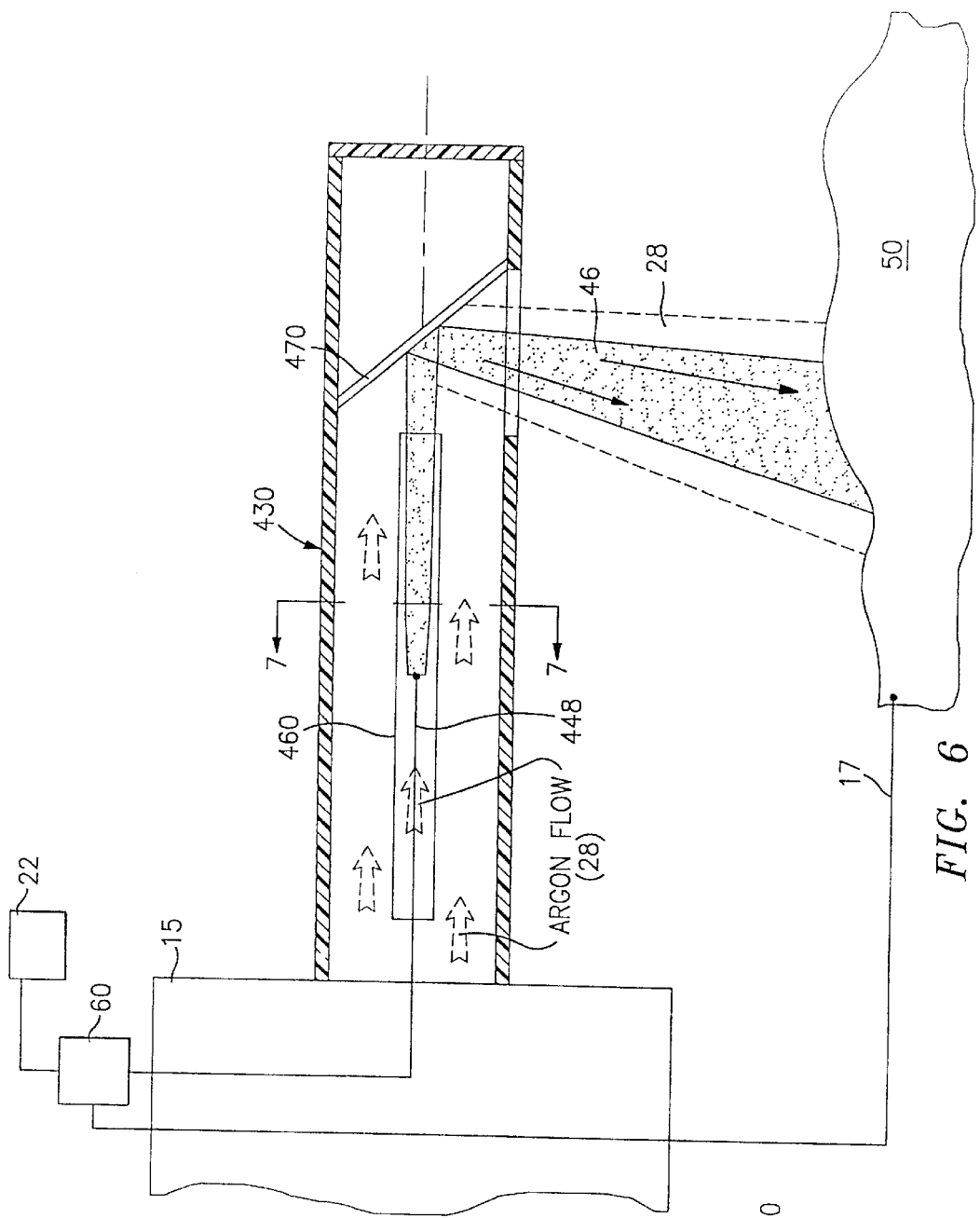
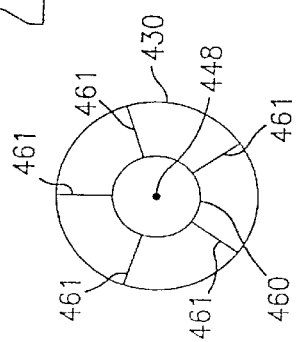
FIG. 6
FIG. 7

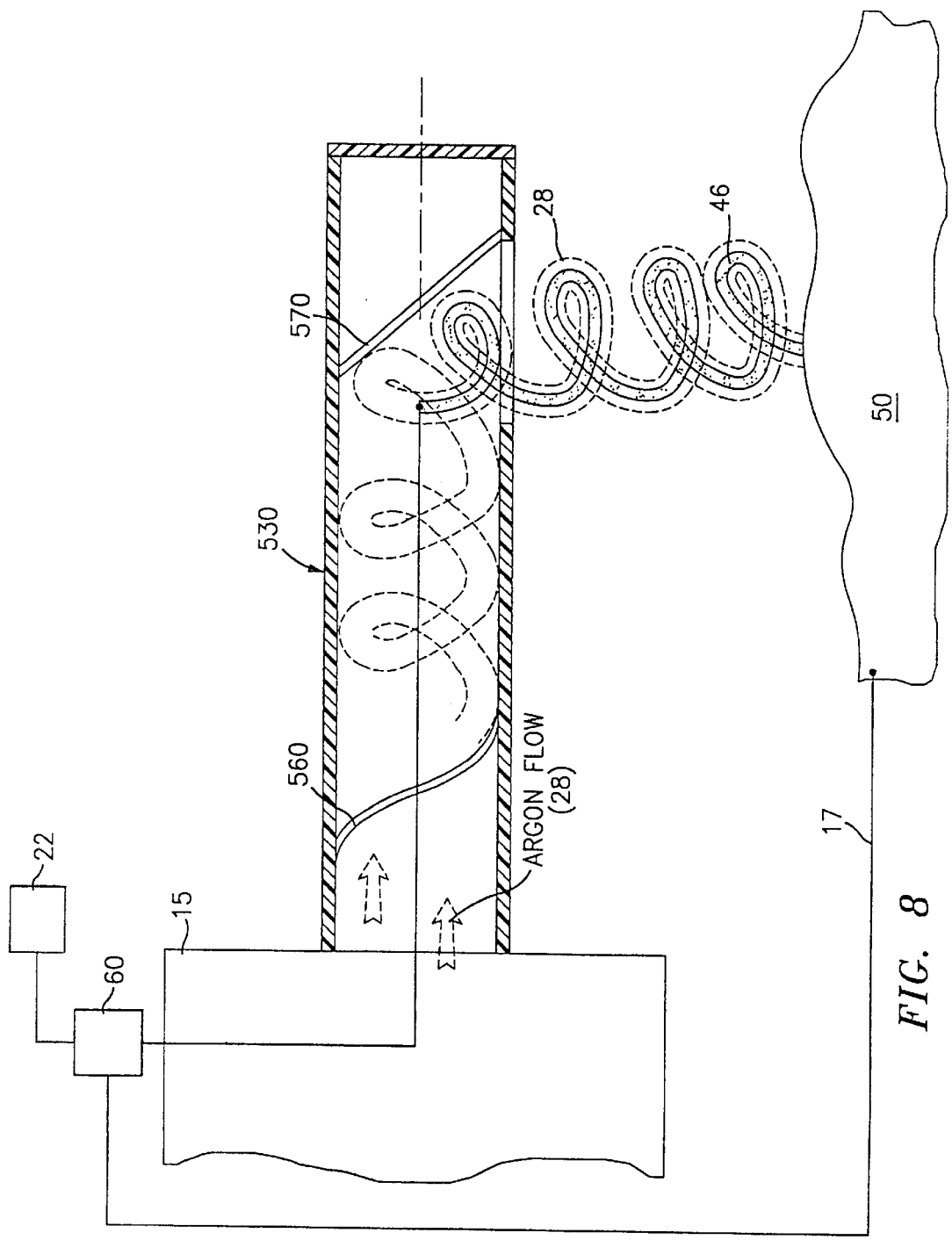

SIDE-FIRE COAGULATOR

TECHNICAL FIELD

The present disclosure relates to devices for use with endoscopes and other electrosurgical instruments for coagulating tissue. More particularly, the present disclosure relates to an argon-enhanced electrosurgical device for coagulating tissue which extends through a working channel of an endoscope.

BACKGROUND OF RELATED ART

Devices for arresting blood loss and coagulating tissue are well known in the art. For example, several prior art instruments employ thermic coagulation (heated probes) to arrest bleeding. However, since the probe must come into close contact with the bleeding tissue, the probe may adhere to the eschar during probe removal possibly causing repeat bleeding. Other instruments direct high frequency electric current through the tissue to stop the bleeding. Again, eschar adherence may also be a problem with these instruments. In both types of instruments, the depth of the coagulation is difficult to control.

U.S. Pat. No. 5,207,675 to Canady attempts to resolve certain of the above-noted problems with respect to the prior art by providing a tube-like coagulation instrument in which an ionizable gas is forced through the instrument and ionized by an electrode prior to the gas exiting the distal end of the instrument towards the bleeding tissue.

U.S. Pat. No. 5,720,745 to Farin et al. discloses a coagulation instrument which extends through a working channel of an endoscope and includes an electrode for ionizing a stream of ionizable gas exiting the distal end of the instrument at a rate of less than about 1 liter/minute. As explained in great detail in the Farin et al. specification, the purpose of discharging the gas at a very low flow rate is to effectively cloud the tissue area and create an ionizable gas "atmosphere" to gently coagulate the tissue. In both of the above patents, the electrodes are not designed to come into direct contact with the tissue.

However, using these instruments to treat certain more tubular sites, e.g., the esophagus and/or colon, is often difficult, impractical and time consuming and may cause unintended collateral damage to the surrounding tissue. For example, the longitudinally oriented instrument fires the ionizable gas and the RF energy in an axial direction from its distal end which, in the case of tubular tissue, would be parallel to the bleeding tissue. Thus, focusing the energy transversely at the bleeding tissue may be very difficult using this instrument and may cause collateral tissue damage.

Thus, a need exists for the development of a new and effective instrument for treating certain more tubular tissue.

SUMMARY

The present disclosure relates to an electrosurgical apparatus for coagulating tissue used in combination with an endoscope. The apparatus includes an elongated flexible tube having a proximal end and a distal end, the proximal end of the tube receives a supply of pressurized ionizable gas and is disposed within a working channel of the endoscope. The tube includes at least one aperture disposed along the periphery of the tube between the proximal and distal ends and an angularly disposed surface which may be a disc located therein for redirecting/reflecting the pressurized ionizable gas through the aperture and at the tissue. An electrode ionizes the pressurized ionizable gas prior to the gas exiting the aperture.

In one embodiment of the present disclosure, the angle of the surface, e.g., disc, is selectively positionable relative to the longitudinal axis of the elongated tube. The surface/disc can also be curved in a convex or concave fashion to affect gas flow. In another embodiment, the tube includes two angularly disposed surfaces/discs and two electrodes for selectively redirecting the gas at different angles at the tissue. Preferably, each of the surfaces/discs is disposed at a different angle relative to the axis of the elongated tube.

A valve can control the amount of gas flowing through the proximal end of the tube and a switch can control the amount of electrical current flowing to the electrode.

BRIEF DESCRIPTION OF THE DRAWINGS

FIG. 6 is an enlarged, side sectional view of another embodiment of the present disclosure showing an elongated ionizing duct located within the tube for ionizing a portion of the ionizable gas flowing therethrough;

FIG. 7 is a cross sectional view of the FIG. 6 embodiment taken along lines 7—7; and FIG. 8 is an enlarged, side sectional view of an alternate embodiment of the present disclosure showing a helically-shaped baffle located within the tube for causing the ionizable gas to flow through the tube with predetermined flow characteristics.

DETAILED DESCRIPTION OF THE PREFERRED EMBODIMENTS

Figure 1:
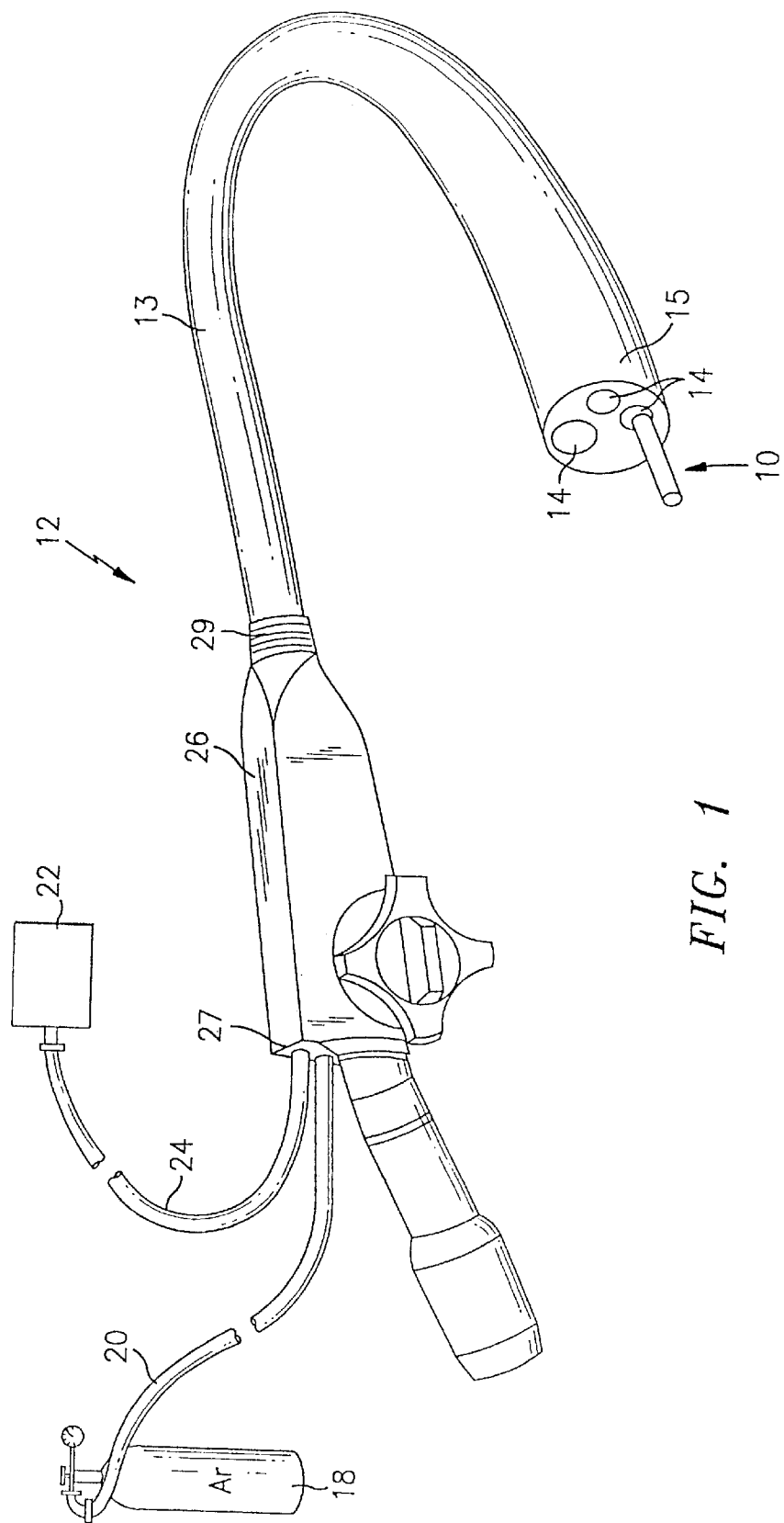
FIG. 1 is a front, perspective view of an electrosurgical instrument shown extending through a working channel of an endoscope.

Referring now to FIG. 1, an argon-enhanced side-fire tissue coagulator generally identified by reference numeral 10 is shown extending through a working channel of an endoscope 12. Preferably, the coagulator 10 can be employed with a variety of different endoscopes such as those manufactured by Olympus, Pentax and Fujinon. As such, only the basic operating features of the endoscope 12 which work in combination with the present disclosure need to be described herein.

For example, endoscope 12 includes a handpiece 26 having a proximal end 27 and a distal end 29. Preferably, the proximal end 27 is mechanically coupled to a supply 18 of pressurized ionizable gas, e.g., inert gas, by way of hose 20 and electrically coupled to an electrosurgical generator 22 by way of cable 24 to supply a source of electrosurgical energy, e.g., high frequency coagulation current, to the endoscope 12. It is envisioned that the electrosurgical generator 22 selectively controls the amount of electrosurgical energy transmitted to an electrode during a surgical procedure. It is also envisioned that the supply of pressurized ionizable gas selectively controls the rate of flow of gas greater than 1 liter per minute.

As shown in FIG. 1, a long, flexible tubular member 13 having one or more of working channels 14 located therein is mechanically coupled to the distal end 29 of the handpiece 26. Preferably, at least one of the working channels 14 is sufficiently dimensioned to receive the coagulator 10 of the present disclosure. Other working channels 14 can be utilized to receive other surgical instruments and accessories such as graspers and biopsy forceps.

Figure 2:
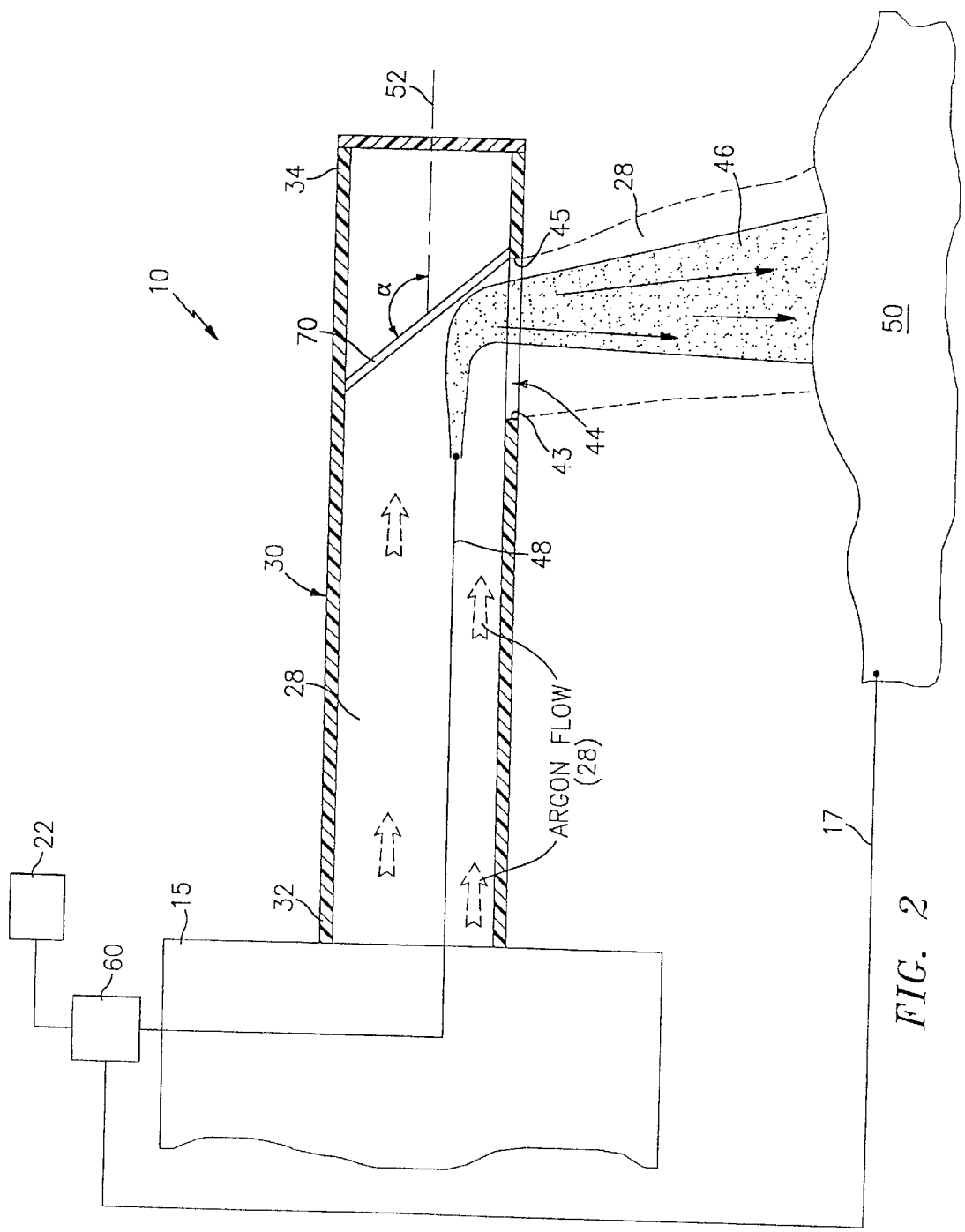
FIG. 2 is an enlarged, side sectional view of one embodiment of the present disclosure showing the ionized gas being reflected off an angularly disposed surface at the tissue.

Turning now to FIG. 2, one preferred embodiment of the coagulator 10 is shown therein and includes an elongated, generally flexible tube 30 having a proximal end 32 which extends through a working channel 14 of the endoscope 12 and a distal end 34 which projects outwardly from the distal end 15 of tube 13. Ionizable gas 28, e.g., argon, is supplied to the proximal end 32 of the coagulator 10 by a gas conduit (not shown) located inside tube 13. Preferably, gas 28 is supplied from source 18 to the coagulator 10 at a selectable, predetermined flow rate. Advantageously, the flow rate of the gas 28 is selectively adjustable and can easily be regulated depending upon a particular purpose or a particular surgical condition.

As mentioned above, the ionizable gas 28 is supplied under pressure to the proximal end 32 of the coagulator 10 and flows generally within the tube 30 in the direction of the arrow towards the distal end 34 of tube 30. A pair of edges or jambs 43 and 45 define a port or aperture 44 which is preferably positioned along the outer periphery of the tube 30 proximate the distal end 34 of the tube 30. It is envisioned that positioning the aperture 44 along the outer periphery of the tube 30 will enable the operator to more effectively coagulate bleeding tissue 50 with more longitudinal-type lesions, i.e., tissue lesions which run parallel to the axial direction endoscope 12, and without causing collateral tissue damage.

Tube 30 also includes a surface, disc or partition 70 which is affixed to tube 30 proximate jamb 45 and extends in an angular direction towards the proximal end 32 of tube 30 to closely abut the inner periphery of tube 30 opposite aperture 44. Preferably, surface/disc 70 is disposed at a predetermined angle alpha ($\alpha$) relative to the longitudinal axis 52 of the endoscope 12 such that surface/disc 50 can redirect the gas 28 flowing through the tube 30 towards aperture 44 at tissue 50. Electrode 48 discharges an electrosurgical current, e.g., radiofrequency (RF), which ionizes the gas 28 prior to the gas 28 being redirected off surface/disc 70 at tissue 50. Preferably, the stream of ionized gas 46 conducts the current to the tissue 50 while effectively scattering blood away from the treatment site allowing the tissue 50 to readily coagulate and arrest bleeding.

Preferably, electrode 48 is connected by way of an electrical conduit (not shown) disposed within tubes 30 and 13 which is ultimately connected to electrosurgical generator 22. Preferably, the electrode 48 is ring or pin-type and is spaced from the aperture 44 such that the electrode 48 cannot come into contact with the tissue 50 during the surgical procedure.

In one particular embodiment of the present disclosure an electrode control mechanism 60 allows an operator to selectively adjust the amount of current flowing through the electrode 48 during surgical conditions. As discussed in more detail below with respect to FIG. 5, control mechanism 60 can be employed to selectively activate and/or deactivate one or more combinations of electrodes 48a, 48b depending upon a particular purpose. A return electrode 17 can also be electrically coupled to control mechanism 60 or electrosurgical generator 22.

Figure 3:
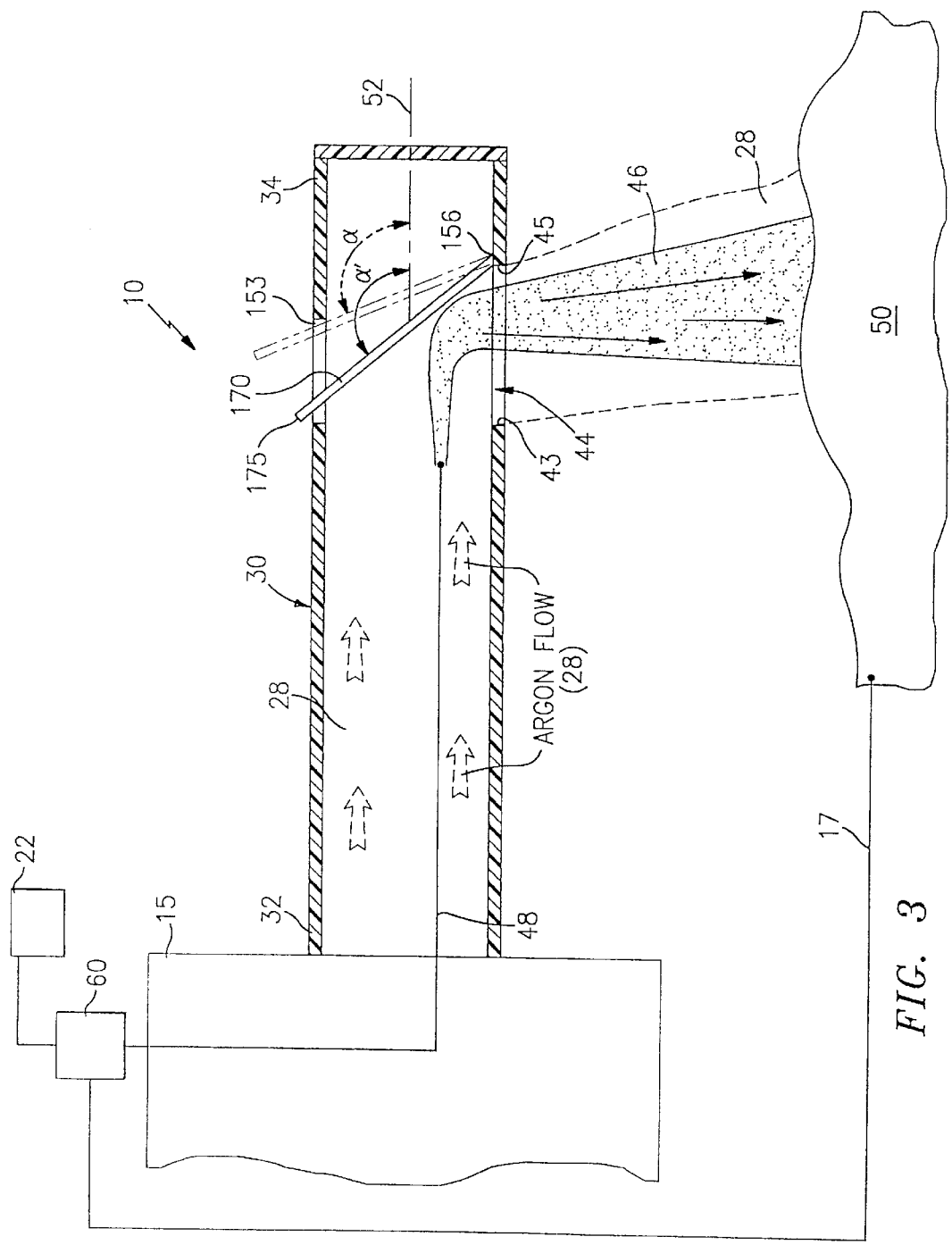
FIG. 3 is an enlarged, side sectional view of another embodiment of the present disclosure wherein the angle of the reflecting surface is selectively positionable within the tube.

FIG. 3 shows an alternate embodiment of the present disclosure wherein the angle $\alpha$ of the surface/disc 170 is selectively positionable. More particularly, surface/disc 170 is affixed to tube 30 about a rotatable hinge 156 which is disposed proximate jamb 45 of aperture 44. Tube 30 also includes a notch 153 which is generally aligned in vertical opposition to aperture 44. Preferably, the upper end of surface/disc 170 includes an angle adjustment tab 175 which slideably engages notch 153 to allow an operator to selectively position the surface/disc 170 at a desired angle a relative to the longitudinal axis of the tube 30. For example, FIG. 3 shows a illustration of the general range of motion of disc 170 from a first position (shown in phantom) having an angle $\alpha$ relative to the axis of tube 30 to a second or subsequent position having an angle $\alpha'$ relative to the axis of tube 30.

It is envisioned that by adjusting the angle $\alpha$ of the surface/disc 170, the angle that the gas 28 reflects off surface/disc 170 and, thus, the angle with respect to the tissue surface or longitudinal axis of the tube at which the ionized gas impinges can be selectively controlled.

Figure 4:
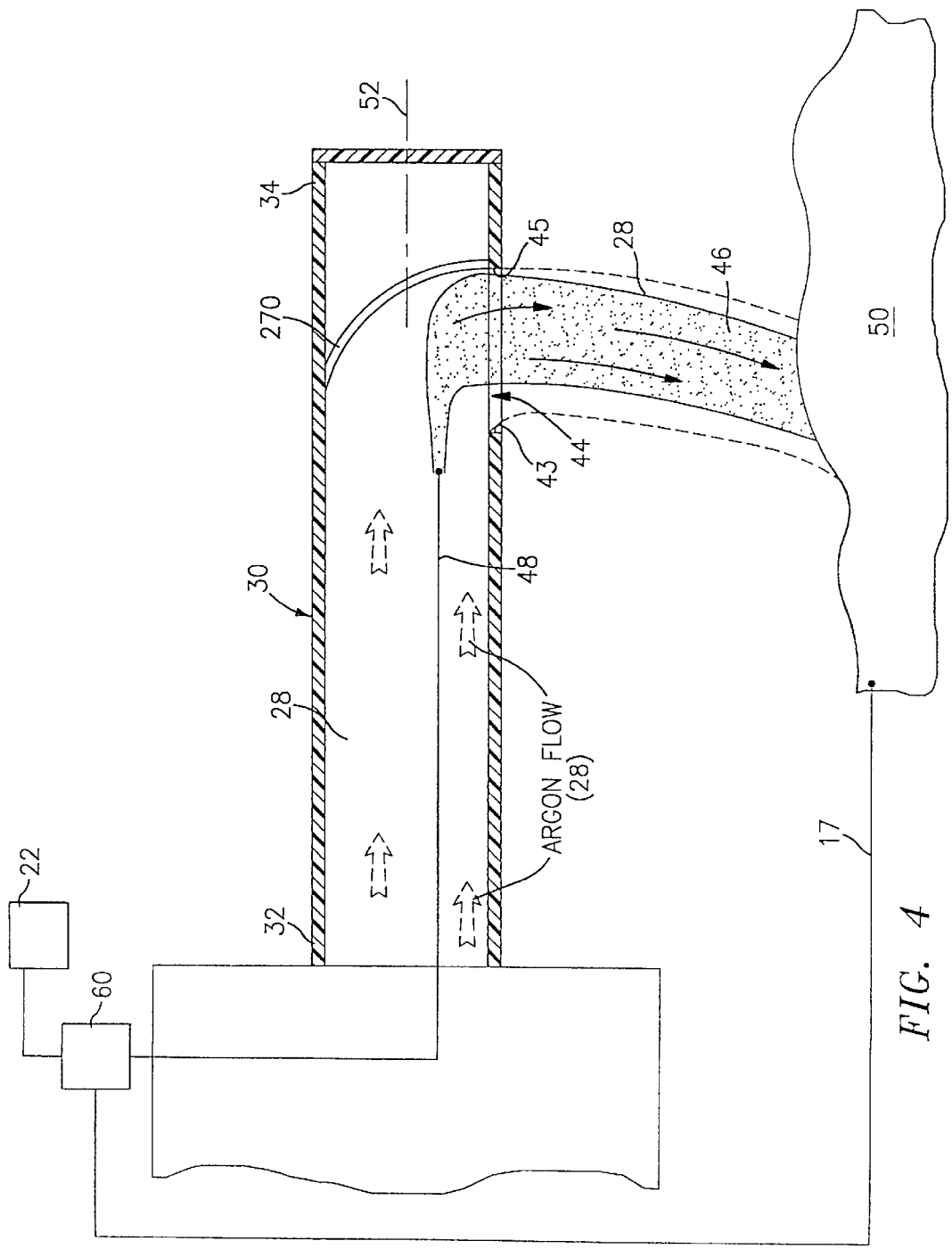
FIG. 4 is an enlarged, side sectional view of another embodiment of the present disclosure showing a curved angularly disposed surface.

FIG. 4 shows another embodiment of the present disclosure whereby the surface/disc 270 is curved such that the gas is reflected off the surface/disc 270 in a smoother, less-turbulent fashion. For example, with the embodiments described in FIGS. 2 and 3, the gas 28 may have a tendency to reflect off disc 70, 170 at such an angle ac that the reflected gas 28 interferes with the gas 28 flowing towards the surface/disc 70, 170, thus creating turbulence. In contrast, it is envisioned that the smooth concave surface of the surface/disc 270 of the FIG. 4 embodiment will redirect the gas 28 in a smoother, more laminar manner. Preferably, the surface/disc 270 is curved in a concave fashion relative to the axis 52 of tube 30, however, in some cases it may be preferable to curve the disc 270 in a convex fashion to create more turbulent gas flow. It is contemplated that the radius of curvature of the surface/disc 270 can be selectively varied to change the flow characteristics of the gas 28 reflecting off the disc 270 towards the tissue.

Figure 5:
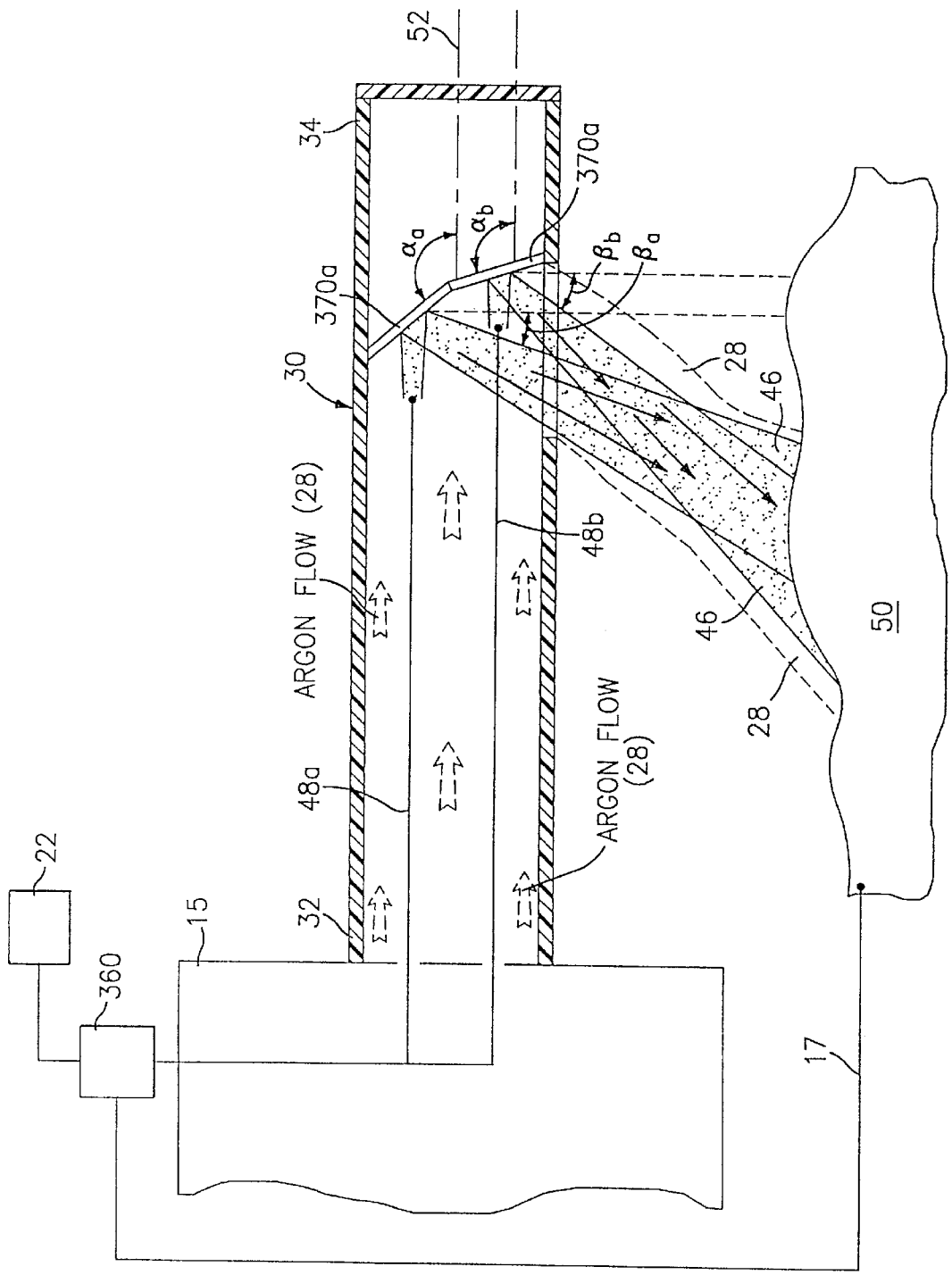
FIG. 5 is an enlarged, side sectional view of another embodiment of the present disclosure showing two electrodes and two angularly disposed surfaces located within the tube which operate in pairs to reflect the ionizable gas at a different angles at the tissue.

FIG. 5 shows another embodiment of the present disclosure whereby the tube 30 includes two surfaces/discs 370a and 370b and two corresponding electrodes 48a and 48b. Preferably, the upper surface/disc 370a is disposed at an angle $\alpha_a$ relative to the axis 52 of the tube 30 and the lower surface/disc 370b is disposed at an angle $\alpha_b$ relative to the axis 52. It is envisioned that the upper surface/disc will deflect a portion of the gas at an angle $\beta_a$ relative to a normal line 53 extending from the tissue 50 and the lower surface/disc will deflect the gas at a less intense angle $\beta_b$ relative to the normal line 53 extending from the tissue 50. Preferably, the electrode 48a, 48b are each disposed proximate the corresponding upper and lower surfaces/discs 370a, 370b, respectively, and a control switch 360 allows the operator to control the activation/deactivation of each electrode 48a, 48b. It is contemplated that by controlling the activation/deactivation of each electrode, the operator can readily alter the intensity of the gas 28 being redirected at the tissue 50.

FIGS. 6 and 7 show yet another alternate embodiment of the present disclosure whereby the tube 430 includes a generally elongated duct or ionizing tube 460 disposed therein which houses and protects electrode 448. Preferably, the ionizing tube 460 is coaxially aligned with axis 452 such that a portion of the gas 28 flowing from the proximal end of tube 430 is redirected through ionizing tube 460. It is envisioned that the electrode 448 ionizes the portion of the gas 28 as it flows through ionizing tube 460 towards surface/disc 470 for deflection at tissue 50. This increases precision and accuracy of the arc and so further protects collateral tissue from being damaged by the electrical discharge from the electrode 448.

FIG. 7 shows a cross-sectional view taken along line 7—7 of FIG. 6 and depicts a series of struts or axles 461 which support ionizing tube 460. The amount and/or pressure of the gas 28 flowing through ionizing tube 460 can be selectively adjustable and/or regulated depending upon a particular purpose or a particular surgical condition. For example, a series of control knobs can be employed to regulate the gas 28 flowing through ionizing tube 460.

FIG. 8 shows yet another alternate embodiment of the present disclosure wherein the gas 28 is caused to flow in a more turbulent manner through tube 530. It is contemplated that many devices may be employed to cause the gas 28 to flow more or less turbulently or with other predetermined flow characteristics through tube 530. For example, FIG. 8 includes a generally helically-shaped baffle 560 which causes gas 28 to swirl within tube 530 prior to the gas 28 being reflected off surface/disc 570.

From the foregoing and with reference to the various figure drawings, those skilled in the art will appreciate that not only can the coagulator 10 of the present disclosure be used to arrest bleeding tissue, but the present disclosure can also be employed for desiccating the surface tissue, eradicating cysts, forming eschars on tumors or thermally marking tissue. Those skilled in the art will also appreciate that certain modifications can also be made to the present disclosure without departing from the scope of the present disclosure.

For example, while several embodiments of the surface/disc 70, 170, 270, 370, 470 and 570 have been described and illustrated herein, other surface/disc structures for reflecting the gas 28 are contemplated, e.g., discs having undulating reflective surfaces, discs having ripples and/or ridges arranged in varying arrays along their reflective surfaces and discs having depressions arranged in varying arrays along their surfaces.

Although it is preferable to utilize argon as the ionizable gas for promulgating coagulation of the tissue 50, in some cases it may be preferably to use another ionizable gas to effect the same or different result.

There have been described and illustrated herein several embodiments of a coagulator for arresting bleeding and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplications of preferred embodiments. Those skilled in the art will envision other modifications within the scope and spirit of the claims appended hereto.

What is claimed is:

1. An electrosurgical apparatus for coagulating tissue, comprising:

an elongated flexible tube having a proximal end and a distal end, said tube comprising at least one aperture located along the periphery of said tube between said proximal and distal ends;

a source for supplying pressurized ionizable gas at a rate of greater than 1 liter per minute to said proximal end of said tube;

an angularly disposed surface located within said tube proximate said aperture for redirecting pressurized ionizable gas through said aperture at said tissue; and at least one electrode for ionizing pressurized ionizable gas prior to pressurized ionizable gas exiting said aperture.

2. An electrosurgical apparatus according to claim 1 wherein the surface is movably mounted such that the angle of said surface relative to the axis of said elongated tube is selectively positionable.

3. An electrosurgical apparatus according to claim 1 further comprising a regulator for regulating the flow of pressurized ionizable gas through said tube.

4. An electrosurgical apparatus according to claim 1 wherein said pressurized ionizable gas is argon.

5. An electrosurgical apparatus according to claim 1 wherein said angularly disposed surface is curved.

6. An electrosurgical apparatus according to claim 1 wherein said tube comprises two angularly disposed surfaces for redirecting pressurized ionizable gas at said tissue.

7. An electrosurgical apparatus according to claim 6 wherein each of said surfaces is disposed at a different angle relative to the axis of said elongated tube.

8. An electrosurgical apparatus according to claim 1 wherein said tube further comprises an elongated duct located therein which redirects a portion of pressurized ionizable gas flowing through said tube to flow through said duct and wherein said electrode for ionizing the pressurized ionizable gas is housed within said duct such that said portion of the pressurized ionizable gas is ionized within said duct prior to said portion of pressurized ionizable gas being redirected off said surface at said tissue.

9. An electrosurgical apparatus according to claim 8 wherein said duct further comprises a valve for regulating the flow of said portion of pressurized ionizable gas through said duct.

10. An electrosurgical apparatus according to claim 1 wherein said tube comprises a baffle disposed therein for causing pressurized ionizable gas to exit said aperture of said tube with predetermined flow characteristics.

11. An electrosurgical apparatus according to claim 10 wherein said baffle is helically-shaped.

\* \* \* \* \*